US011298420B2

(12) United States Patent
Cantwell (10) Patent No.: US 11,298,420 B2
(45) Date of Patent: Apr. 12, 2022

(54) ARMED ONCOLYTIC VIRUSES (71) Applicant: Memgen, LLC, Houston, TX (US)

(72) Inventor: Mark J. Cantwell, San Diego, CA (US)

(73) Assignee: MEMGEN, LLC, Houston, TX (US)

(*) Notice: Subject to any disclaimer, the term of this patent is extended or adjusted under 35 U.S.C. 154(b) by 0 days.

(21) Appl. No.: 15/843,603

(22) Filed: Dec. 15, 2017

(65) Prior Publication Data
US 2018/0169241 A1 Jun. 21, 2018

Related U.S. Application Data (60) Provisional application No. 62/437,474, filed on Dec. 21, 2016.

(51) Int. Cl.
A61K 39/42 (2006.01)
A61K 38/17 (2006.01)
C07K 14/705 (2006.01)
A61P 35/00 (2006.01)
A61K 39/00 (2006.01)

(52) U.S. Cl.
CPC .............. A61K 39/42 (2013.01); A61K 38/17 (2013.01); A61P 35/00 (2018.01); C07K 14/70578 (2013.01); A61K 2039/5256 (2013.01); C12N 2710/16032 (2013.01); Y02A 50/30 (2018.01)

(58) Field of Classification Search
None
See application file for complete search history.

(56) References Cited

U.S. PATENT DOCUMENTS

| 7,928,213 | B2 * | 4/2011 | Prussak | C07K 14/70575 435/252.3 |
|---|---|---|---|---|
| 2003/0220473 | A1 | 11/2003 | Prussak et al. | |
| 2005/0048476 | A1 | 3/2005 | Prussak et al. | |
| 2015/0232880 | A1 * | 8/2015 | Hemminki | A61K 35/17 514/44 R |
| 2016/0289645 | A1 * | 10/2016 | Tufaro | A61K 35/761 |
| 2017/0327588 | A1 * | 11/2017 | Baca | C07K 16/30 |

FOREIGN PATENT DOCUMENTS

| WO | 98000026061 | A2 | 6/1998 |
| WO | 03000099340 | A1 | 4/2003 |
| WO | 20080070743 | A2 | 6/2008 |
| WO | 2017079202 | A1 | 5/2017 |
| WO | 20170079297 | A1 | 5/2017 |

OTHER PUBLICATIONS

Fernandes et al. Growth Inhibition of Human Multiple Myeloma Cells by an Oncolytic Adenovirus Carrying the CD40 Ligand Transgene. Clin Cancer Res. Aug. 1, 2009;15(15):4847-56.*
Macrophage inflammatory protein. Downloaded online from Wikipedia on May 21, 2019.*
Singh et al. Intratumoral CD40 activation and checkpoint blockade induces systemic anti-melanoma immunity that eradicates disseminated tumors [abstract]. In: Proceedings of the Second CRI-CIMT-EATI-AACR International Cancer Immunotherapy Conference: Translating Science into Survival; Sep. 25-28, 2016; New York, NY.*
Dias et al. Targeted cancer immunotherapy with oncolytic adenovirus coding fora fully human monoclonal antibody specific for CTLA-4. Gene Therapy (2012) 19, 988-998.*
Ali, et al., "The Use of DNA viruses as vectors for gene therapy;" Review—Gene Therapy; (1994); vol. 1; pp. 367-384.
Aruffo, et al., "The CD40 Ligand, gp39, is Defective in Activated T Cells from Patients with X-Linked Hyper-IgM Syndrome;" Cell, vol. 72, pp. 291-300 (1993).
Cantwell, et al., "Adenovirus Vector Infection of Chronic Lymphocytic Leukemia B Cells;" Blood, vol. 88, No. 12 (1996) pp. 4676-4683.
PCT Search Report from International Application No. PCT/US2017/067137; dated Apr. 5, 2018; 8 pgs.
Written Opinion from International Application No. PCT/US2017/067137; dated Apr. 5, 2018; 11 pgs.
Banchereau, et al., "The CD40 Antigen and its Ligand;" Annu. Rev. Immunol.; vol. 12 (1994) pp. 881-922.
Cantwell, et al., "Acquired CD40-ligand deficiency in chronic lymphocytic leukemia;" Nature Medicine, vol. 3, No. 9 (1997) pp. 984-989.
Castle, et al., "Regulation of expression of the ligand for CD40 on T helper lymphocytes;" The Journal of Immunology; vol. 151; pp. 1777-1788; No. 4; (1993).
Cooper, Mark J, "Noninfectious Gene Transfer and Expression Systems for Cancer Gene Therapy;" Seminars in Oncology, vol. 23, No. 1 (February), pp. 172-187; (1996).
Glorioso, et al., "Development and Application of Herpes Simplex Virus Vectors for Human Gene Therapy;" Annu. Rev. Microbiol; vol. 49; pp. 675-710; (1995).
Gruss, et al., "The TNF ligand superfamily and its relevance for human diseases;" Cytokines and Molecular Therapy; vol. 1; pp. 75-105; (1995).
Hermann, et al., "Expression of a 32-kDa ligand for the CD40 antigen on activated human T lymphocytes;" Eur. J. Immunol.; vol. 23; pp. 961-964; (1993).
Kohlapp, et al., "Molecular Pathways: Mechanism of Action for Talimogene Laherparepvec, a New Oncolytic Virus Immunotherapy;" Clin Cancer Res; vol. 22; No. 5 (2016) Published OnlineFirst Dec. 30, 2015; DOI: 10.1158/1078-0432. CCR-15-2667.
Kohn, Donald B., "The current status of gene therapy using hematopoietic stem cells;" Current Opinion in Pediatrics; vol. 7; pp. 56-63; (1995).
Korthauer, et al., "Defective expression of T-cell CD40 ligand causes X-linked immunodeficiency with hyper-IgM;" Nature; vol. 361; pp. 539-541; (1993).

(Continued)

Primary Examiner — Nianxiang Zou
(74) Attorney, Agent, or Firm — Williams Morgan, P.C.

(57) ABSTRACT

Disclosed are oncolytic viruses comprising chimeric human/mouse CD40 ligands. The chimeric human/mouse CD40 ligand may be MEM40. The oncolytic virus may be replication competent. The oncolytic virus may be an oncolytic herpes simplex virus. Also disclosed are methods comprising administering an oncolytic virus armed with at least one chimeric human/mouse CD40 ligand, for example MEM40, to a patient suffering from cancer.

43 Claims, 2 Drawing Sheets
Specification includes a Sequence Listing.

(56) References Cited

OTHER PUBLICATIONS

Laman, et al., "Functions of CD40 and its Ligand, gp39 (CD40L);" Critical Reviews in Immunology; vol. 16; Issue 1; pp. 59-108; (1996).
Lawler, et al., "Oncolytic Viruses in Cancer Treatment A Review;" JAMA Oncol.; vol. 3, No. 6; pp. 841-849; (2017).
Locksley, et al., "The TNF and TNF Receptor Superfamilies: Integrating Mammalian Biology;" Cell; vol. 104; pp. 487-501; (2001).
Macejak, et al., "Internal initiation of translation mediated by the 5' leader of a cellular mRNA;" Nature; vol. 353; pp. 90-94; (1991).
Pelletier, et al.; "Cap-Independent Translation of Poliovirus mRNA is Conferred by Sequence Elements within the 5' Noncoding Region;" Molecular and Cellular Biology; vol. 8; No. 3; pp. 1103-1112; (1988).
Randrianarison-Jewtoukoff, et al., "Recombinant Adenoviruses as Vaccines;" Biologicals; vol. 23; pp. 145-157; (1995).
Ranheim, et al., "Activated T Cells Induce Expression of B7/BB1 on Normal or Leukemic B Cells through a CD40-dependent Signal;" J. Exp. Med.; vol. 177; pp. 925-935; (1993).
Ranheim, et al., "Tumor Necrosis Factor-Facilitates Induction of CD80 (B7-1) and CD54 on Human B Cells by Activated T Cells: Complex Regulation by IL-4, IL-10, and CD40L;" Cellular Immunology; vol. 161; pp. 226-235; (1995).
Roizman, Bernard, "The function of herpes simplex virus genes: A primer for genetic engineering of novel vectors;" Proc. Natl. Acad. Sci. USA; vol. 93; pp. 11307-11312; (1996).
Roy, et al., "The regulation of the expression of gp39, the CD40 ligand, on normal and cloned CD4+ T cells.;" J Immunol; vol. 151; pp. 2497-2510; (1993).
Russell, Stephen J., "Replicating vectors for cancer therapy: a question of strategy;" Cancer Biology; vol. 5; pp. 437-443; (1994).
Russell, et al., "Oncolytic Virotherapy;" Nat Biotechnol; vol. 30; No. 7; pp. 658-670; (2014).
Shaughnessy, et al., "Parvoviral Vectors for the Gene Therapy of Cancer;" Seminars in Oncology; vol. 23; No. 1; pp. 159-171; (19966).
Singh, et al., "Intratumoral CD40 activation and checkpoint blockade induces T cell-mediated eradication of melanoma in the brain;" Nature Communications; vol. 8:1447; pp. 1-10; www.nature.com/naturecommunications.
Smith, et al., "Gene delivery systems for use in gene therapy: an overview of quality assurance and safety issues;" Gene Therapy; vol. 3; pp. 190-200; (1996).
Sunshine, et al., "PD-1/PD-L1 inhibitors;" Curr Opin Pharmacol; vol. 23; pp. 32-38; (2015).
Van Kooten, et al., "CD40-CD40 ligand;" Journal of Leukocyte Biology; vol. 67; No. 1; pp. 2-17 (2017).
Vile, et al., "Retroviruses as vectors;" British Medical Bulletin; vol. 51; No. 1; pp. 12-30; (1995).
Woll, et al., "Gene therapy for lung cancer;" Annals of Oncology; vol. 6 (Suppl. 1); pp. 73-77; (1995).
Castro, et al., "Gene Immunotherapy of Chronic Lymphocytic Leukemia: A Phase 1 Study of Intranodally Injected Adenovirus Expressing a Chimeric CD154 Molecule;" Cancer Research; vol. 72; No. 12; pp. 2937-2948; (2012.
Fukuhara, et al., "Oncolytic virus therapy: A new era of cancer treatment at dawn;" Cancer Science; vol. 1007; No. 10; pp. 1373-1379; (2016).
Loskog, Angelica, "Immunostimulatory Gene Therapy Using Oncolytic Viruses as Vehicles;" Viruses; vol. 7; pp. 5780-5791; (2015).
Singh, et al., "Abstract B022: Intratumoral CD40 activation and checkpoint blockade induces systemic anti-melanoma immunity that eradicates disseminated tumors;" Abstract Second CRI-CIMT-EATI-AACR International Cancer Immunotherapy Conference: Translating Science into Survival; vol. 4; Issue 11; pp. 25-28; (2016).
Urquiza, et al.,"Intratumoral Injection of Ad-ISF35 (Chimeric CD154) Breaks Tolerance and Induces Lymphoma Tumor Regression;" Human Gene Therapy; vol. 26; pp. 14-25; (2015).
De Graff, J.F.; et al.; Armed Oncolytic Viruses: A kick-start for anti-tumor immunity; Department of Viroscilience, Erasmus MC, Rotterdam, The Netherlands; Cytokine and Growth Factor Reviews 41 (2018) 28-39.

\* cited by examiner

SEQUENCE LISTING

```
<160> NUMBER OF SEQ ID NOS: 12

<210> SEQ ID NO 1
<211> LENGTH: 783
<212> TYPE: DNA
<213> ORGANISM: Artificial Sequence
<220> FEATURE:
<223> OTHER INFORMATION: chimeric human/mouse CD40 ligand

<400> SEQUENCE: 1
atgatagaaa catacagcca accttccccc agatccgtgg caactggact tccagcgagc        60
atgaagattt ttatgtattt acttactgtt ttccttatca cccaaatgat tggatctgtg       120
```

-continued

```
cttttttgctg tgtatcttca tagaagattg ataaggtcg aagaggaagt aaaccttcat    180
gaagattttg tattcataaa aaagctaaag agatgcaaca aaggagaagg atctttatcc    240
ttgctgaact gtgaggagat gagaaggcaa tttgaagacc ttgtcaagga tataacgtta    300
aacaaagaag agaaaaaaga aaacagcttt gaaatgcaaa gaggtgatga ggatcctcaa    360
attgcagcac acgttgtaag cgaagccaac agtaatgcag catccgttct acagtgggcc    420
aagaaaggat attataccat gaaaagcaac ttggtaaccc tggaaaatgg gaaacagctg    480
acggttaaaa gacaaggact ctattatatc tatgctcaag tcaccttctg ctctaatcgg    540
gagccttcga gtcaacgccc attcatcgtc ggcctctggc tgaagcccag cagtggatct    600
gagagaatct tactcaaggc ggcaaatacc cacagttcct cccagctttg cgagcagcag    660
tctgttcact gggcggagt gtttgaatta caaccaggtg cttcggtgtt tgtcaatgtg    720
actgatccaa gccaagtgag ccatggcact ggcttcacgt cctttggctt actcaaactc    780
tga                                                                 783
```

<210> SEQ ID NO 2
<211> LENGTH: 759
<212> TYPE: DNA
<213> ORGANISM: Artificial Sequence
<220> FEATURE:
<223> OTHER INFORMATION: chimeric human/mouse CD40 ligand
<400> SEQUENCE: 2

```
atgatcgaaa catacaacca aacttctccc cgatctgcgg ccactggact gcccatcagc     60
atgaaaattt ttatgtattt acttactgtt tttcttatca cccagatgat tgggtcagca    120 cttttttgctg tgtatcttca tagaaggctg acaagatag aagatgaaag gaatcttcat    180
gaagattttg tattcatgaa aacgatacag agatgcaaca caggagaaag atccttatcc    240
ttactgaact gtgaggagat taaaagccag tttgaaggct tgtgaagga tataatgtta    300 aacaaagagg agacgaagaa agatgaggat cctcaaattg cagcacacgt tgtaagcgaa    360
gccaacagta atgcagcatc cgttctacag tgggccaaga aggatatta ccatgaaa     420 agcaacttgg taaccctgga aaatgggaaa cagctgacgg ttaaaagaca aggactctat    480
tatatctatg ctcaagtcac cttctgctct aatcgggagc cttcgagtca acgccattc     540 atcgtcggcc tctggctgaa gcccagcagt ggatctgaga gaatcttact caaggcggca    600
aatacccaca gttcctccca gctttgcgag cagcagtctg ttcacttggg cggagtgttt    660
gaattacaac caggtgcttc ggtgtttgtc aatgtgactg atccaagcca agtgagccat    720
ggcactggct tcacgtcctt tggcttactc aaactctga                          759
```

<210> SEQ ID NO 3
<211> LENGTH: 783
<212> TYPE: DNA
<213> ORGANISM: Artificial Sequence
<220> FEATURE:
<223> OTHER INFORMATION: chimeric human/mouse CD40 ligand
<400> SEQUENCE: 3

```
atgatagaaa catacagcca accttccccc agatccgtgg caactggact tccagcgagc     60
atgaagattt ttatgtattt acttactgtt ttccttatca cccaaatgat tggatctgtg    120 cttttttgctg tgtatcttca tagaagattg ataaggtcg aagaggaagt aaaccttcat    180
gaagattttg tattcataaa aaagctaaag agatgcaaca aaggagaagg atctttatcc    240
ttgctgaact gtgaggagat gagaaggcaa tttgaagacc ttgtcaagga tataacgtta    300
```

```
aacaaagaag agaaaaaaga aaacagcttt gaaatgcaaa gaggtgatga ggatcctcaa    360
attgcagcac acgttgtaag cgaagccaac agtaatgcag catccgttct acagtgggcc    420
aagaaaggat attataccat gaaaagcaac ttggtaaccc tggaaaatgg gaaacagctg    480
acggttaaaa gacaaggact ctattatatc tatgctcaag tcaccttctg ctctaatcgg    540
gaggcttcga gtcaagcccc attcatcgtc ggcctctggc tgaagcccag cagtggatct    600
gagagaatct tactcaaggc ggcaaatacc cacagttcct cccagctttg cgagcagcag    660
tctgttcact tgggcggagt gtttgaatta caaccaggtg cttcggtgtt tgtcaatgtg    720
actgatccaa gccaagtgag ccatggcact ggcttcacgt cctttggctt actcaaactc    780
tga                                                                  783

<210> SEQ ID NO 4
<211> LENGTH: 759
<212> TYPE: DNA
<213> ORGANISM: Artificial Sequence
<220> FEATURE:
<223> OTHER INFORMATION: chimeric human/mouse CD40 ligand

<400> SEQUENCE: 4
atgatcgaaa catacaacca aacttctccc cgatctgcgg ccactggact gcccatcagc     60
atgaaaattt ttatgtattt acttactgtt tttcttatca cccagatgat tgggtcagca    120 cttttttgctg tgtatcttca tagaaggctg acaagatag aagatgaaag gaatcttcat    180 gaagatttg tattcatgaa acgatacag agatgcaaca caggagaaag atccttatcc    240
ttactgaact gtgaggagat taaaagccag tttgaaggct tgtgtaagga tataatgtta    300
aacaaagagg agacgaagaa agatgaggat cctcaaattg cagcacacgt tgtaagcgaa    360
gccaacagta atgcagcatc cgttctacag tgggccaaga aaggatatta ccatgaaaa    420 agcaacttgg taaccctgga aaatgggaaa cagctgacgg ttaaaagaca aggactctat    480
tatatctatg ctcaagtcac cttctgctct aatcgggagg cttcgagtca gccccattc    540 atcgtcggcc tctggctgaa gcccagcagt ggatctgaga gaatcttact caaggcggca    600
aatacccaca gttcctccca gctttgcgag cagcagtctg ttcacttggg cggagtgttt    660
gaattacaac aggtgcttc ggtgtttgtc aatgtgactg atccaagcca agtgagccat    720
ggcactggct tcacgtcctt tggcttactc aaactctga                           759

<210> SEQ ID NO 5
<211> LENGTH: 783
<212> TYPE: DNA
<213> ORGANISM: Artificial Sequence
<220> FEATURE:
<223> OTHER INFORMATION: chimeric human/mouse CD40 ligand

<400> SEQUENCE: 5
atgatagaaa catacagcca accttccccc agatccgtgg caactggact tccagcgagc     60
atgaagattt ttatgtattt acttactgtt ttccttatca cccaaatgat tggatctgtg    120
ctttttgctg tgtatcttca tagaagattg gataaggtcg aagaggaagt aaaccttcat    180 gaagatttg tattcataaa aaagctaaag agatgcaaca aggagaagg atctttatcc    240 ttgctgaact gtgaggagat gagaaggcaa tttgaagacc ttgtcaagga tataacgtta    300
aacaaagaag agaaaaaaga aaacagcttt gaaatgcaaa gaggtgatga ggatcctcaa    360
attgcagcac acgttgtaag cgaagccaac agtaatgcag catccgttct acagtgggcc    420
aagaaaggat attataccat gaaaagcaac ttggtaaccc tggaaaatgg gaaacagctg    480
```

```
acggttaaaa gacaaggact ctattatatc tatgctcaag tcaccttctg ctctaatcgg    540
gaggcttcga gtcaagcccc attcatcgtc ggcctctggc tgaagcccag cagtggatct    600
gagagaatct tactcaaggc ggcaaatacc cacagttcct cccagctttg cgagcagcag    660
tctattcact gggcggagt gtttgaatta caaccaggtg cttcggtgtt tgtcaatgtg     720
actgatccaa gccaagtgag ccatggcact ggcttcacgt cctttggctt actcaaactc    780
tga                                                                  783

<210> SEQ ID NO 6
<211> LENGTH: 759
<212> TYPE: DNA
<213> ORGANISM: Artificial Sequence
<220> FEATURE:
<223> OTHER INFORMATION: chimeric human/mouse CD40 ligand

<400> SEQUENCE: 6
atgatcgaaa catacaacca aacttctccc cgatctgcgg ccactggact gcccatcagc     60
atgaaaattt ttatgtattt acttactgtt tttcttatca cccagatgat tgggtcagca    120 cttttttgctg tgtatcttca tagaaggctg acaagatag aagatgaaag gaatcttcat    180
gaagattttg tattcatgaa aacgatacag agatgcaaca caggagaaag atccttatcc    240
ttactgaact gtgaggagat taaaagccag tttgaaggct tgtgaagga tataatgtta    300 aacaaagagg agacgaagaa agatgaggat cctcaaattg cagcacacgt tgtaagcgaa    360
gccaacagta atgcagcatc cgttctacag tgggccaaga aggatatta ccatgaaaa    420 agcaacttgg taaccctgga aaatgggaaa cagctgacgg ttaaaagaca aggactctat    480
tatatctatg ctcaagtcac cttctgctct aatcgggagg cttcgagtca agccccattc    540
atcgtcggcc tctggctgaa gcccagcagt ggatctgaga gaatcttact caaggcggca    600 ataccaca gttcctccca gctttgcgag cagcagtcta ttcacttggg cggagtgttt    660
gaattacaac caggtgcttc ggtgtttgtc aatgtgactg atccaagcca agtgagccat    720
ggcactggct tcacgtcctt tggcttactc aaactctga                           759

<210> SEQ ID NO 7
<211> LENGTH: 783
<212> TYPE: DNA
<213> ORGANISM: Artificial Sequence
<220> FEATURE:
<223> OTHER INFORMATION: chimeric human/mouse CD40 ligand

<400> SEQUENCE: 7
atgatagaaa catacagcca accttccccc agatccgtgg caactggact tccagcgagc     60
atgaagattt ttatgtattt acttactgtt ttccttatca cccaaatgat tggatctgtg    120 cttttttgctg tgtatcttca tagaagattg gataaggtcg aagaggaagt aaaccttcat    180
gaagattttg tattcataaa aaagctaaag agatgcaaca aaggagaagg atctttatcc    240
ttgctgaact gtgaggagat gagaaggcaa tttgaagacc ttgtcaagga taacgtta    300 aacaaagaag agaaaaaaga aaacagcttt gaaatgcaaa gaggtgatga ggatcctcaa    360
attgcagcac acgttgtaag cgaagccaac agtaatgcag catccgttct acagtgggcc    420
aagaaaggat attataccat gaaaagcaac ttggtaaccc tggaaaatgg gaaacagctg    480
acggttaaaa gacaaggact ctattatatc tatgctcaag tcaccttctg ctctaatcgg    540
gaggcttcga gtcaagcccc attcatcgtc ggcctctggc tgaagcccag cagtggatct    600
gagagaatct tactcaaggc ggcaaatacc cacagttccg ccaagccttg cgggcagcag    660
```

```
tctattcact tgggcggagt gtttgaatta caaccaggtg cttcgtgttt tgtcaatgtg    720
actgatccaa gccaagtgag ccatggcact ggcttcacgt cctttggctt actcaaactc    780
tga                                                                  783
```

<210> SEQ ID NO 8
<211> LENGTH: 759
<212> TYPE: DNA
<213> ORGANISM: Artificial Sequence
<220> FEATURE:
<223> OTHER INFORMATION: chimeric human/mouse CD40 ligand

<400> SEQUENCE: 8

```
atgatcgaaa catacaacca aacttctccc cgatctgcgg ccactggact gcccatcagc     60
atgaaaattt ttatgtattt acttactgtt tttcttatca cccagatgat gggtcagca    120 cttttttgctg tgtatcttca tagaaggctg acaagatag aagatgaaag gaatcttcat   180
gaagattttg tattcatgaa acgatacag agatgcaaca caggagaaag atccttatcc    240
ttactgaact gtgaggagat taaaagccag tttgaaggct tgtgtaagga tataatgtta    300
aacaaagagg agacgaagaa agatgaggat cctcaaattg cagcacacgt tgtaagcgaa    360
gccaacagta atgcagcatc cgttctacag tgggccaaga aggatatta ccatgaaa      420 agcaacttgg taaccctgga aaatgggaaa cagctgacgg ttaaaagaca aggactctat    480
tatatctatg ctcaagtcac cttctgctct aatcggagg cttcgagtca gccccattc     540 atcgtcggcc tctggctgaa gcccagcagt ggatctgaga atcttact caaggcggca     600 aatacccaca gttccgccaa gccttgcggg cagcagtcta ttcacttggg cggagtgttt    660
gaattacaac aggtgcttc ggtgtttgtc aatgtgactg atccaagcca agtgagccat     720
ggcactggct tcacgtcctt tggcttactc aaactctga                           759
```

<210> SEQ ID NO 9
<211> LENGTH: 783
<212> TYPE: DNA
<213> ORGANISM: Artificial Sequence
<220> FEATURE:
<223> OTHER INFORMATION: chimeric human/mouse CD40 ligand

<400> SEQUENCE: 9

```
atgatagaaa catacagcca accttccccc agatccgtgg caactggact tccagcgagc     60
atgaagattt ttatgtattt acttactgtt ttccttatca cccaaatgat ggatctgtg    120 cttttttgctg tgtatcttca tagaagattg ataaggtcg aagaggaagt aaaccttcat    180
gaagattttg tattcataaa aaagctaaag agatgcaaca aaggagaagg atctttatcc    240
ttgctgaact gtgaggagat gagaaggcaa tttgaagacc ttgtcaagga tataacgtta    300
aacaaagaag agaaaaaga aaacagcttt gaaatgcaaa gaggtgatga ggatcctcaa    360
attgcagcac acgttgtaag cgaagccaac agtaatgcag catccgttct acagtgggcc    420
aagaaaggat attataccat gaaaagcaac ttggtaaccc tggaaaatgg gaaacagctg    480
acggttaaaa gacaaggact ctattatatc tatgctcaag tcaccttctg ctctaatcgg    540
gagccttcga gtcaacgccc attcatcgtc ggctctggc tgaagcccag cagtggatct    600
gagagaatct tactcaaggc ggcaaatacc cacagttcct cccagctttg cgagcagcag    660
tctattcact gggcggagt gtttgaatta caaccaggtg cttcggtgtt tgtcaatgtg     720
actgatccaa gccaagtgag ccatggcact ggcttcacgt cctttggctt actcaaactc    780
tga                                                                  783
```

<210> SEQ ID NO 10
<211> LENGTH: 759
<212> TYPE: DNA
<213> ORGANISM: Artificial Sequence
<220> FEATURE:
<223> OTHER INFORMATION: chimeric human/mouse CD40 ligand

<400> SEQUENCE: 10

```
atgatcgaaa catacaacca aacttctccc cgatctgcgg ccactggact gcccatcagc      60
atgaaaattt ttatgtattt acttactgtt tttcttatca cccagatgat tgggtcagca     120
cttttttgctg tgtatcttca tagaaggctg acaagatag aagatgaaag gaatcttcat     180
gaagattttg tattcatgaa aacgatacag agatgcaaca caggagaaag atccttatcc     240
ttactgaact gtgaggagat taaaagccag tttgaaggct tgtgtaagga tataatgtta     300
aacaaagagg agacgaagaa agatgaggat cctcaaattg cagcacacgt tgtaagcgaa     360
gccaacagta atgcagcatc cgttctacag tgggccaaga aggatatta ccatgaaa      420
agcaacttgg taaccctgga aaatgggaaa cagctgacgg ttaaaagaca aggactctat     480
tatatctatg ctcaagtcac cttctgctct aatcgggagc cttcgagtca acgcccattc     540
atcgtcggcc tctggctgaa gcccagcagt ggatctgaga gaatcttact caaggcggca     600
aatacccaca gttcctccca gctttgcgag cagcagtcta ttcacttggg cggagtgttt     660
gaattacaac aggtgcttc ggtgtttgtc aatgtgactg atccaagcca agtgagccat     720
ggcactggct tcacgtcctt tggcttactc aaactctga                            759
```

<210> SEQ ID NO 11
<211> LENGTH: 783
<212> TYPE: DNA
<213> ORGANISM: Artificial Sequence
<220> FEATURE:
<223> OTHER INFORMATION: chimeric human/mouse CD40 ligand

<400> SEQUENCE: 11

```
atgatagaaa cattacagcca accttccccc agatccgtgg caactggact tccagcgagc      60
atgaagattt ttatgtattt acttactgtt ttccttatca cccaaatgat tggatctgtg     120
cttttttgctg tgtatcttca tagaagattg ataaggtcg aagaggaagt aaaccttcat     180
gaagattttg tattcataaa aaagctaaag agatgcaaca aaggagaagg atctttatcc     240
ttgctgaact gtgaggagat gagaaggcaa tttgaagacc ttgtcaagga tataacgtta     300
aacaaagaag agaaaaaaga aaacagcttt gaaatgcaaa gaggtgatga ggatcctcaa     360
attgcagcac acgttgtaag cgaagccaac agtaatgcag catccgttct acagtgggcc     420
aagaaaggat attataccat gaaaagcaac ttggtaaccc tggaaaatgg gaaacagctg     480
acggttaaaa gacaaggact ctattatatc tatgctcaag tcaccttctg ctctaatcgg     540
gagccttcga gtcaacgccc attcatcgtc ggcctctggc tgaagcccag cagtggatct     600
gagagaatct tactcaaggc ggcaaatacc cacagttccg ccaagccttg cgggcagcag     660
tctattcact gggcggagt gtttgaatta caaccaggtg cttcggtgtt tgtcaatgtg     720
actgatccaa gccaagtgag ccatggcact ggcttcacgt cctttggctt actcaaactc     780
tga                                                                    783
```

<210> SEQ ID NO 12
<211> LENGTH: 759
<212> TYPE: DNA
<213> ORGANISM: Artificial Sequence

```
<220> FEATURE:
<223> OTHER INFORMATION: chimeric human/mouse CD40 ligand

<400> SEQUENCE: 12
atgatcgaaa catacaacca aacttctccc cgatctgcgg ccactggact gcccatcagc      60
atgaaaattt ttatgtattt acttactgtt tttcttatca cccagatgat tgggtcagca     120 cttttttgctg tgtatcttca tagaaggctg gacaagatag aagatgaaag gaatcttcat    180
gaagattttg tattcatgaa aacgatacag agatgcaaca caggagaaag atccttatcc    240
ttactgaact gtgaggagat taaaagccag tttgaaggct ttgtgaagga tataatgtta    300
aacaaagagg agacgaagaa agatgaggat cctcaaattg cagcacacgt tgtaagcgaa    360
gccaacagta atgcagcatc cgttctacag tgggccaaga aaggatatta tccatgaaa    420 agcaacttgg taaccctgga aaatgggaaa cagctgacgg ttaaaagaca aggactctat    480
tatatctatg ctcaagtcac cttctgctct aatcgggagc cttcgagtca acgcccattc    540
atcgtcggcc tctggctgaa gcccagcagt ggatctgaga gaatcttact caaggcggca    600
aatacccaca gttccgccaa gccttgcggg cagcagtcta ttcacttggg cggagtgttt    660
gaattacaac caggtgcttc ggtgtttgtc aatgtgactg atccaagcca agtgagccat    720
ggcactggct tcacgtcctt tggcttactc aaactctga                          759
```

ARMED ONCOLYTIC VIRUSES

This application claims priority from U.S. provisional application 62/437,474, filed on Dec. 21, 2016, which is incorporated herein by reference.

BACKGROUND OF THE INVENTION

The present invention relates generally to the field of virology, immunology, and medicine. More particularly, it concerns compositions of oncolytic viral vectors for the treatment of cancer.

DESCRIPTION OF RELATED ART

Oncolytic viruses are a class of cancer therapeutic agents with a dual mechanism of action: 1) tumor cell killing through selective viral replication in tumor cells resulting in direct tumor lysis and 2) induction of systemic anti-tumor immunity by releasing antigens from destroyed tumor cells. Both native and genetically modified viruses are in development. The US Food and Drug Administration (FDA) approved in 2015 the first oncolytic virus, talimogene laherparepvec (IMLYGIC®, Amgen Inc., Thousand Oaks, Calif.), a genetically modified herpes virus encoding granulocyte-macrophage colony-stimulating factor (GM-CSF) for the local treatment of melanoma, as described by Kohlhapp et. al. 2016 Clinical Cancer Research. However, melanoma is only one of many types of cancer. Moreover, herpes virus is only one of many viruses that may be used for treatment of cancer. Likewise, GM-CSF is only one of many compounds under investigation for use in cancer therapies.

Accordingly, there remains a need for oncolytic viral vectors for the treatment of cancer.

SUMMARY OF THE INVENTION

The following presents a simplified summary of the disclosure in order to provide a basic understanding of some aspects of the disclosure. This summary is not an exhaustive overview of the disclosure. It is not intended to identify key or critical elements of the disclosure or to delineate the scope of the disclosure. Its sole purpose is to present some concepts in a simplified form as a prelude to the more detailed description that is discussed later.

In some embodiments, the present disclosure relates to oncolytic viruses comprising chimeric human/mouse CD40 ligands.

In some embodiments, the present disclosure relates to a method comprising administering, to a mammal suffering from a tumor, a composition comprising an oncolytic virus comprising at least one chimeric human/mouse CD40 ligand.

In either embodiment, the chimeric human/mouse CD40 ligand may be selected from ISF30-ISF41, such as ISF35 (MEM40).

Transgenes encoding ISF30-ISF35, including ISF35 (MEM40), have previously been transfected into a non-oncolytic, non-replicating adenovirus. However, such transgenes have never been transfected into an oncolytic virus, particularly including an oncolytic herpes simplex virus.

BRIEF DESCRIPTION OF THE DRAWINGS

The disclosure may be understood by reference to the following description taken in conjunction with the accompanying drawings, in which.

DESCRIPTION OF ILLUSTRATIVE EMBODIMENTS

Various illustrative embodiments of the disclosure are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present subject matter will now be described with reference to the attached figures. Various structures are schematically depicted in the drawings for purposes of explanation only and so as to not obscure the present disclosure with details that are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

Oncolytic Virus Overview

Multiple biologic properties may be considered in selection or design of a therapeutic oncolytic virus for desired therapeutic activity, including: selective targeting of cancer cells for infection through natural tropism of cell surface proteins or by engineering virus to directly target cancer cells; selective replication in cancer cells; attenuation of viral pathogenesis; enhancing lytic activity; modification of the antiviral immune response that can lead to rapid clearance of virus; and modification of systemic anti-tumor immunity through genetic modification of viruses to incorporate cytokines, immune agonists, or immune checkpoint blockers.

There are a broad range of oncolytic virus types being considered as anti-cancer agents, including but not limited to: herpes simplex virus (HSV), adenovirus, vaccinia virus, poxvirus, coxsackievirus, poliovirus, measles virus, parvovirus, reovirus, Seneca valley virus, Newcastle disease virus, retrovirus, vesicular stomatitis virus, paramyxovirus, Sindbis virus, myxoma virus, Maraba virus, influenza virus, mumps virus, arenavirus, and Semliki Forest virus. Exemplary oncolytic viruses are discussed by Russell et. al. 2014 Nature Biotechnology and Lawler et. al. 2017 JAMA Oncology.

Replication competent oncolytic herpes simplex viruses have several properties that make them ideal for therapeutic applications, including: 1) their ability to infect a wide variety of tumors; 2) their inherent cytolytic nature; 3) their well characterized large genome (152 Kb) that provides ample opportunity for genetic manipulations wherein many of the non-essential genes (up to 30 kb) can be replaced by therapeutic genes; 4) their ability to remain as episomes that avoid insertional mutagenesis in infected cells; and 5) the availability of anti-viral drugs (e.g., valaciclovir) to keep in check possible undesirable replication.

CD40 Agonist Overview

Though not to be bound by theory, the success of cancer immunotherapy may depend on enhancing tumor-specific CD8+ T cell immunity since CD8+ T cells are strongly associated with direct tumor killing and patient survival. Thus, therapeutic modalities that promote CD8+ T cell responses are a goal in cancer immunotherapy drug development.

The CD40 receptor is a member of tumor necrosis factor receptor family and is expressed by B cells, professional antigen-presenting cells, and non-immune cells and tumors (van Kooten et. al. 2000 Journal of Leukocyte Biology). Activation of tumor-specific T cell responses requires activation of the CD40 receptor on antigen presenting cells. CD4+ T cells enhance CD8+ T cell priming by licensing dendritic cells (DCs) via CD40-CD154 interactions. In addition, CD40-CD154 interactions prevent the CD8+ T cell response from diminishing prematurely. Therefore, CD40 activation through CD154 is a requisite step for inducing effective antigen-specific CD8 T cell immunity against pathogens and tumor (Singh et. al. 2017 Nature Communications). In this regard, CD40-agonist therapies, such as antibodies or cognate CD40 ligand (CD40L) proteins, appear as a promising strategy for cancer immunotherapy.

ISF35 Overview

ISF35 (which may also be referred to herein as "MEM40") is a chimeric human/mouse CD40 ligand that has 92% amino acid sequence homology with human CD40L. See, U.S. Pat. No. 7,495,090, herein incorporated by reference). ("CD40 ligand" and "CD40L" may be used interchangeably herein, and may also be referred to as "CD154"). Specifically, domains I, II and III—the regions that contain the intracellular, intra-membrane, and proximal extracellular domains, respectively, of this molecule—have been fully humanized. In domain IV, which contains the CD40 binding portion of the molecule, only those murine domains necessary for optimum CD40 ligand expression in cells are retained. ISF35 (MEM40) is fully humanized at the 3' end of the molecule where antibody binding neutralizes the activity of the murine CD154 (CD40 ligand) when administered to humans.

Besides ISF35, workers for the present assignee have invented a panel of chimeric CD40 ligand constructs (ISF30 through ISF41). ISF35 is a specific chimerical CD40 ligand in the panel with the most nonclinical and clinical studies performed to date.

Illustrative Embodiments

In some embodiments, the present disclosure relates an oncolytic virus comprising at least one chimeric human/mouse CD40 ligand.

In still other embodiments, the present disclosure relates to replication competent oncolytic viruses comprising chimeric human/mouse CD40 ligands.

In one embodiment, the present disclosure relates to replication competent oncolytic herpes simplex viruses comprising chimeric human/mouse CD40 ligands.

In still other embodiments, the present disclosure relates to replication competent oncolytic herpes simplex virus comprising both a chimeric human/mouse CD40 ligand and one or more additional immunodulatory or therapeutic genes, such as a cytokine (e.g., GM-CSF, TNFα), an interleukin (e.g., IL-2, IL-12), a chemokine (e.g., RANTES), a macrophage inflammatory protein (e.g., MIP-3), a checkpoint inhibitor (e.g., anti-PD-1, anti-CDTA4, and anti-PD-L1), or another immunomodulatory protein (e.g., OX40 ligand).

The present disclosure provides for oncolytic viruses, including herpes simplex virus (HSV), adenovirus, vaccinia virus, poxvirus, coxsackievirus, poliovirus, measles virus, parvovirus, reovirus, Seneca valley virus, Newcastle disease virus, retrovirus, vesicular stomatitis virus, reovirus, paramyxovirus, Sindbis virus, myxoma virus, Maraba virus, influenza virus, measles virus, mumps virus, arenavirus, and Semliki Forest virus encoding a CD40 agonist.

Viral regions may be altered for multiple purposes to impart desirable therapeutic properties. Non-limiting examples of therapeutic properties may include enhanced viral replication and spread, enhanced oncolysis, preferential targeting of tumor cells versus normal cells, enhanced immune activation, and protection of virus from the host immune system. Viral regions for the purposes described above may be either eliminated (complete or partial deletions), made non-functional, modified to attenuate function, or substituted by other sequences. Oncolytic viruses may also be altered to include one or more heterologous genes encoding therapeutic protein(s) and/or immunomodulatory protein(s). In a particular embodiment, an oncolytic virus comprises a heterologous gene encoding a CD40 agonist.

In some embodiments, the present disclosure provides herpes simplex virus with improved capabilities for both immune-mediated and viralytic destruction of tumor cells. Here herpes simplex virus strains may be constructed from HSV1 or HSV2 wherein genes encoding ICP34.5 and ICP45 have been rendered nonfunctional. Furthermore, the herpes simplex virus strains may carry a gene encoding a chimeric human/mouse CD40 ligand immune agonist protein either alone or in combination with one or more additional therapeutic gene(s).

In other embodiments, the present disclosure relates to a method comprising administering to a patient suffering from a tumor a composition comprising an oncolytic virus comprising at least one chimeric human/mouse CD40 ligand.

In the embodiments, the chimeric human/mouse CD40 ligand may be selected from ISF30-ISF41, of which MEM40 (ISF35) is a member.

In some embodiments, the present disclosure provides for oncolytic viruses, including herpes simplex virus (HSV), adenovirus, vaccinia virus, poxvirus, coxsackievirus, poliovirus, measles virus, parvovirus, reovirus, Seneca valley virus, Newcastle disease virus, retrovirus, vesicular stomatitis virus, reovirus, paramyxovirus, Sindbis virus, myxoma virus, Maraba virus, influenza virus, measles virus, mumps virus, arenavirus, and Semliki Forest virus encoding a CD40 agonist.

In a particular embodiment, the present disclosure relates to an oncolytic herpes simplex virus comprising a sequence encoding a CD40 agonist operatively linked to a transcriptional control element.

In a particular embodiment, the oncolytic herpes simplex virus may be genetically modified to incorporate a chimeric human/mouse CD40 ligand transgene.

Genetic modification of an oncolytic virus to incorporate a CD40 ligand transgene, including a chimeric human/mouse CD40 ligand transgene, may be performed using techniques known to the person of ordinary skill in the art. The oncolytic virus would contain the chimeric human/mouse CD40 ligand transgene with necessary regulatory elements (e.g., cytomegalovirus (CMV) promoter or alternative promoter; polyadenylation domain) to allow for chimeric human/mouse CD40 ligand gene transcription and expression of the chimeric human/mouse CD40 ligand polypeptide in infected cells.

In one embodiment, the chimeric human/mouse CD40 ligand may be selected from the group consisting of ISF30 (SEQ ID NO:1), ISF31 (SEQ ID NO:2), ISF32 (SEQ ID NO:3), ISF33 (SEQ ID NO:4), ISF34 (SEQ ID NO:5), ISF35 (MEM40) (SEQ ID NO:6), ISF36 (SEQ ID NO:7), ISF37 (SEQ ID NO:8), ISF38 (SEQ ID NO:9), ISF39 (SEQ ID NO:10), ISF40 (SEQ ID NO:11), and ISF41 (SEQ ID NO:12).

Polypeptide sequences and exemplary nucleic acid sequences encoding the polypeptide sequences of ISF30, ISF32, ISF34, ISF36, ISF38, and ISF40 are disclosed in U.S. Pat. No. 7,928,213, which is hereby incorporated by reference herein. Polypeptide sequences and exemplary nucleic acid sequences encoding the polypeptide sequences of ISF31, ISF33, ISF35, ISF37, ISF39, and ISF41 are disclosed in U.S. Pat. No. 7,495,090, which is hereby incorporated by reference herein.

In a further embodiment, the chimeric human/mouse CD40 ligand may be ISF35 (MEM40) (SEQ ID NO:6).

The heterologous chimeric human/mouse CD40 ligand can be inserted at any nonessential location in the oncolytic virus. In one embodiment, the oncolytic virus remains replication competent.

In one embodiment, the oncolytic virus comprising at least one chimeric human/mouse CD40 ligand may be an ISF35-HSV oncolytic virus. Use of HSV may be desirable given the prior FDA approval of this virus type, as well as additional properties of HSV that make HSV attractive for drug development, as described above.

The HSV may be a non-laboratory virus strain. In one embodiment, the oncolytic herpes simplex virus is derived from an HSV JS1 strain.

In a particular embodiment, the heterologous chimeric human/mouse CD40 ligand nucleic acid is inserted into the ICP34.5 gene encoding region of the oncolytic herpes simplex virus, rendering the ICP34.5 gene nonfunctional. The ICP34.5 region is nonessential for viral replication (U.S. Pat. No. 7,223,593, herein incorporated by reference). Furthermore, deletion or inactivation of the ICP34.5 gene reduces HSV neurovirulence and provides tumor-selective replication. (Roizman 1996 Proceedings of the National Academy of Sciences)

In a particular embodiment, the ICP47 gene is also deleted from the oncolytic herpes simplex virus encoding a chimeric human/mouse CD40 ligand. Deletion of ICP47 prevents HSV from blocking antigen presentation and results in earlier and increased US11 expression (Roizman 1996 Proceedings of the National Academy of Sciences).

Viral regions altered for the purposes described above may be either eliminated completely or partly, or made nonfunctional by substitution or insertion of other gene sequences, in particular MEM40.

The oncolytic virus may be genetically modified further to improve one or more properties for use in treatment of cancer, including, selective replication in cancer cells; attenuation of viral pathogenesis; enhancing lytic activity; modification of the antiviral immune response that can lead to rapid clearance of virus; and modification of viral-induced systemic anti-tumor immunity.

In embodiments wherein the oncolytic virus has an RNA genome, the gene encoding the chimeric human/mouse CD40 ligand may be rendered suitable for expression from an RNA viral genome prior to insertion of the gene into the genome. For example, the gene encoding the chimeric human/mouse CD40 ligand may undergo replacement of thymine with uracil to facilitate expression from an RNA viral genome. Other modifications that may be suitable for such embodiments will be known to the person of ordinary skill in the art.

In one embodiment, the present disclosure relates to a method comprising administering, to a mammal suffering from a tumor, a composition comprising an oncolytic virus comprising at least one chimeric human/mouse CD40 ligand. The oncolytic virus may be replication competent. In particular embodiments, the oncolytic virus and the at least one chimeric human/mouse CD40 ligand may be as described above. In one embodiment, the oncolytic virus comprising at least one chimeric human/mouse CD40 ligand may be an HSV-MEM40 replication competent herpes simplex virus.

In another embodiment, the oncolytic virus comprising at least one chimeric human/mouse CD40 ligand may also encode one or more additional therapeutic protein(s). Multiple heterologous genes can be incorporated into oncolytic virus genomes. In a particular embodiment, the second immunomodulatory protein is human GM-CSF.

Regardless of oncolytic virus species and chimeric human/mouse CD40 ligand(s) chosen, the oncolytic virus comprising at least one chimeric human/mouse CD40 ligand may be used for the treatment of cancer, whereby the virus is administered by intratumoral injection. However, intravenous delivery may also be considered.

Though not to be bound by theory, an oncolytic virus comprising at least one chimeric human/mouse CD40 ligand may have dual mechanisms of action: 1) tumor cell killing through selective viral replication of the oncolytic virus in cancer cells and 2) induction of systemic anti-tumor immunity generated by both viral immune induction and CD40 ligand immune activation.

Regulatory Elements

Expression cassettes included in vectors useful in the present disclosure contain (in a 5'-to-3' direction) a transcriptional promoter operably linked to a protein-coding sequence, splice signals including intervening sequences, and a transcriptional termination/polyadenylation sequence. The promoters and enhancers that control the transcription of protein encoding genes in eukaryotic cells are composed of multiple genetic elements. The cellular machinery gathers and integrates the regulatory information conveyed by each element, allowing different genes to evolve distinct, often complex patterns of transcriptional regulation. A promoter used in the context of the present disclosure includes constitutive, inducible, and tissue-specific promoters.

Promoter/Enhancers

Chimeric human/mouse CD40 ligand nucleic acid expression may be under the control of a promoter functional in mammalian cells, such as human tumor cells. In one embodiment, the promoter directing expression of a chimerical human/mouse CD40 ligand is a cytomegalovirus (CMV) promoter.

The expression constructs provided herein comprise a promoter to drive expression of the programming genes. A promoter generally comprises a sequence that functions to position the start site for RNA synthesis. The best example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. These are typically in the region 30 to 110 bp upstream of the start site, although promoters have been shown to contain functional elements downstream of the start site as well. To bring a coding sequence "under the control of" a promoter, one positions the 5-prime end of the transcription initiation site of the transcriptional reading frame "downstream" of (i.e., 3-prime of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be naturally associated with a nucleic acid sequence and obtained by isolating the 5-prime non-coding sequences located upstream of the coding segment and/or exon. Such a promoter can be referred to as "endogenous." Similarly, an enhancer may be naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression.

One can employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression. The promoters employed may be constitutive, tissue-specific, inducible, and/or useful under the appropriate conditions to direct high-level expression of the introduced DNA segment, such as is advantageous in the large-scale production of recombinant proteins and/or peptides. The promoter may be heterologous or endogenous.

Non-limiting examples of promoters include early or late viral promoters, such as SV40 early or late promoters, cytomegalovirus (CMV) immediate early promoters, Rous Sarcoma Virus (RSV) early promoters, and eukaryotic cell promoters.

Initiation Signals and Linked Expression

A specific initiation signal may also be used in the expression constructs provided in the present disclosure for efficient translation of coding sequences. These signals include the ATG initiation codon or adjacent sequences. Exogenous translational control signals, including the ATG initiation codon, may need to be provided. One of ordinary skill in the art would be readily capable of providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements are used to create multigene, or polycistronic, messages. IRES elements can bypass the ribosome scanning model of 5-prime methylated Cap dependent translation and begin translation at internal sites (Pelletier et. al. 1988 Molecular and Cellular Biology). IRES elements from two members of the picornavirus family (polio and encephalomyocarditis) have been described (Pelletier et. al. 1988 Molecular and Cellular Biology), as well as an IRES from a mammalian message (Macejak et. al. 1991 Nature). IRES elements can be linked to heterologous open reading frames. Multiple open reading frames can be transcribed together, each separated by an IRES, creating polycistronic messages. The IRES element enables each open reading frame to be accessible to ribosomes for efficient translation. Multiple genes can be efficiently expressed using a single promoter/enhancer to transcribe a single message (U.S. Pat. Nos. 5,925,565 and 5,935,819, each herein incorporated by reference).

Methods of Viral Modification

The various genes referred to may be rendered functionally inactive by several techniques well known in the art, including gene deletion(s), substitution(s), or insertion(s). Similarly, immunomodulatory genes, including MEM40 and GM-CSF, may be inserted into the viral genome by methods well known to those skilled in the art. These types of modifications in the herpes simplex virus may be made by homologous recombination methods. For example, HSV genomic DNA may be transfected together with a plasmid vector comprising mutated sequence flanked by homologous HSV sequences, resulting in DNA recombination and substitution of the parent HSV genomic DNA region with new mutated sequence region.

Exemplary constructions of replication competent oncolytic viruses comprising chimeric human/mouse CD40 ligands are shown in FIGS. 1-4.

Figure 1:
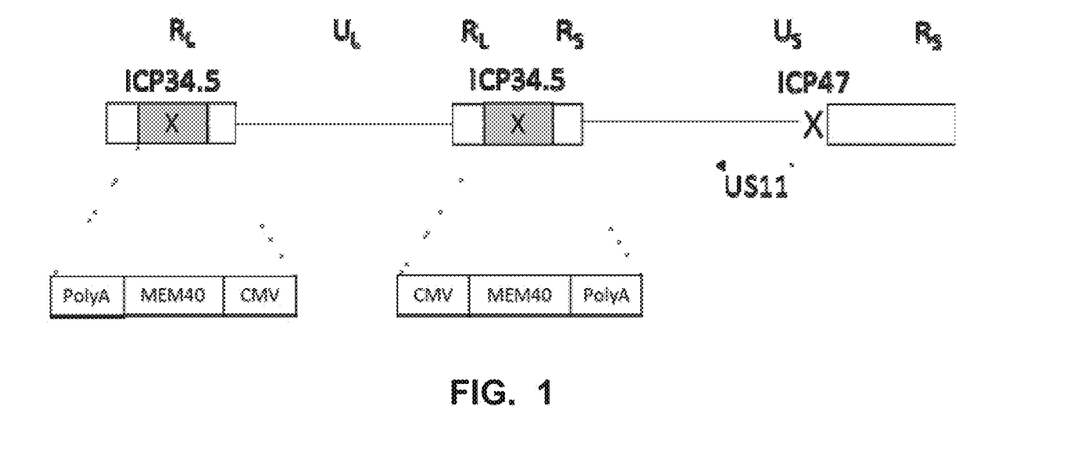
FIG. 1 schematically represents the construction of HSV-MEM40, a replication competent herpes simplex virus expressing MEM40, in accordance with embodiments herein.

Turning to FIG. 1, an HSV-MEM40, a replication competent herpes simplex virus expressing MEM40, may be constructed as schematically represented. A MEM40 expression cassette that includes a MEM40 cDNA flanked upstream by a CMV promoter and downstream by a bovine growth hormone polyadenylation signal (PolyA) is inserted into the ICP34.5 gene encoding regions. In addition, the ICP47 gene was deleted.

Figure 2:
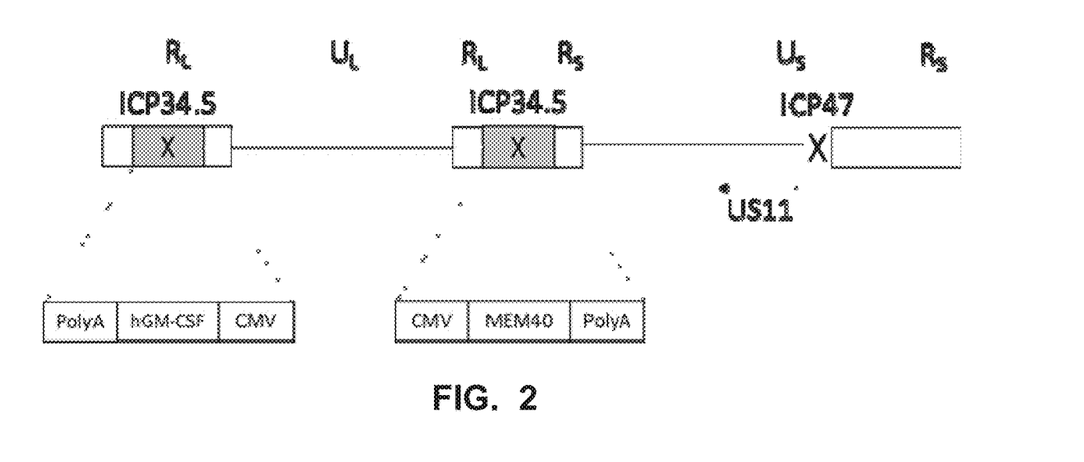
FIG. 2 schematically represents the construction of HSV-MEM40-GMCSF, a replication competent herpes simplex virus expressing both MEM40 and human GM-CSF, in accordance with embodiments herein.

FIG. 2 schematically represents the construction of HSV-MEM40-GMCSF, a replication competent herpes simplex virus expressing both MEM40 and human GM-CSF. Construction is similar to HSV-MEM40 (FIG. 1), but with the addition of a human GM-CSF expression cassette inserted in one ICP34.5 encoding region and the MEM40 expression cassette in the other ICP34.5 gene encoding region.

Figure 3:
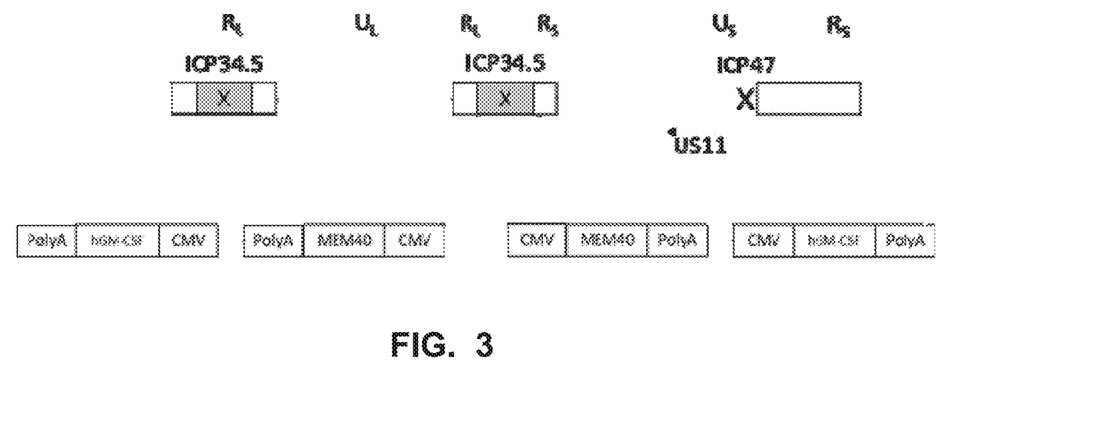
FIG. 3 schematically represents the construction of HSV-MEM40-GMCSF, a replication competent herpes simplex virus expressing both MEM40 and human GM-CSF, in accordance with embodiments herein.

FIG. 3 schematically represents the construction of HSV-MEM40-GMCSF, a replication competent herpes simplex virus expressing both MEM40 and human GM-CSF. Construction is similar to HSV-MEM40 (FIG. 1), but with the addition of a human GM-CSF expression cassette inserted in tandem with the MEM40 expression cassette into both ICP34.5 gene encoding regions.

Figure 4:
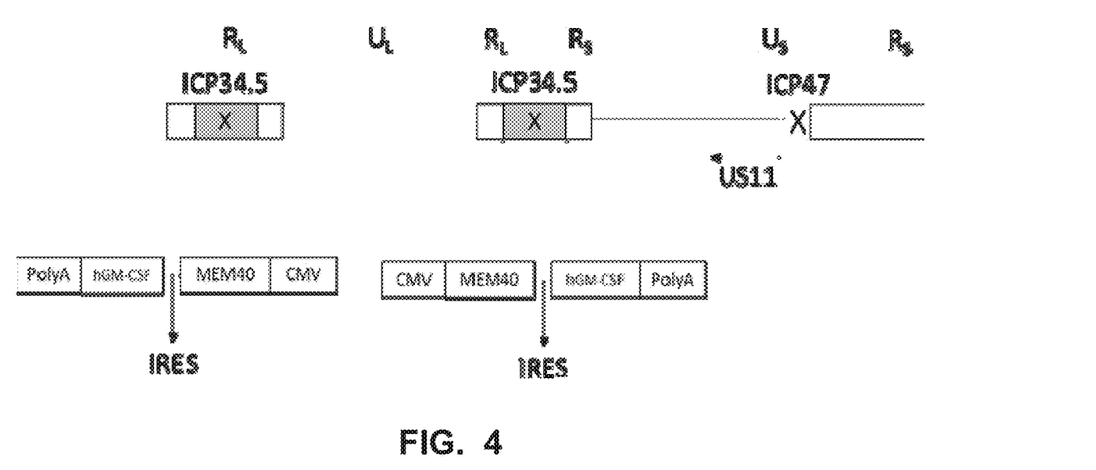
FIG. 4 schematically represents the construction of HSV-MEM40-IRES-GMCSF, a replication competent herpes simplex virus expressing both MEM40 and human GM-CSF, wherein the genes are separated by an internal ribosomal entry site (IRES) sequence, in accordance with embodiments herein.

FIG. 4 schematically represents the construction of HSV-MEM40-IRES-GMCSF, a replication competent herpes simplex virus expressing both MEM40 and human GM-CSF. Construction is similar to HSV-MEM40-GMCSF (FIG. 2), with the difference that the human GM-CSF and MEM40 genes are part of the same expression cassette for co-expression of each protein using a single CMV promoter. The GM-CSF and MEM40 genes are separated with an internal ribosomal entry site (IRES) sequence for co-expression of multiple transgenes.

Methods of Screening of Viruses for Therapeutic Utility

Oncolytic viruses of the disclosure, or variants or derivatives thereof, can be evaluated for their therapeutic utility by examination of their lytic potential in tumor cells. The tumor cells may include primary tumor cells derived from patient biopsies or surgical resections. Alternatively, the tumor cells may include tumor cell lines. The cytolytic activity of viruses of the disclosure can be determined in tumor cell lines in vitro by infection of cells with serial dilutions of virus and determining the cytolytic potency (i.e. $IC_{50}$). Particular methods for determining cytolytic activity may include but are not limited MTS, MTT, and ATP colorimetric assays which are well known in the art.

The therapeutic index, a comparison of the amount of a therapeutic agent that causes the therapeutic effect to the amount that causes toxicity, of an oncolytic virus of the disclosure may be calculated by comparing the cytolytic potency of the virus in a tumor cell line with the cytolytic potency in a matched normal cell.

The oncolytic viruses of the disclosure can be further evaluation for therapeutic utility by evaluation of their ability to infect tumor cells and/or normal cells and express a functional chimeric human/mouse CD40 ligand polypeptide encoded by the oncolytic virus. The chimeric human/mouse CD40 ligand expressed on the cell surface of infected cells can be evaluated by flow cytometry using antibodies that specifically recognize human or mouse CD40 antibody binding regions. Chimeric human/mouse CD40 ligand functional activity can also be examined using an in vitro bioassay wherein tumor or normal cells infected with an oncolytic virus encoding a chimeric human/mouse CD40 ligand are mixed with effector cells stably expressing the CD40 receptor fused with a downstream luciferase response element and measuring induced luciferase expression.

The oncolytic viruses of the disclosure can further be evaluated for their ability to target tumor cell growth and the capacity to reduce tumorigenesis or tumor cell burden in mice harboring naturally derived or transplanted tumors in syngeneic or xenogeneic tumor models in mice. Tumor burden as measured by tumor size, immune protection from tumor rechallenge, and animal survival, are all possible measures of therapeutic utility and animal tumor models.

Methods of Treatment and Administration

Regardless of the oncolytic virus and chimeric human/mouse CD40 ligand(s) chosen, the oncolytic virus comprising at least one chimeric human/mouse CD40 ligand may be used for the treatment of cancer, whereby the virus is administered by intratumoral injection. However, other routes of delivery may also be considered, including intravenously, intraperitoneally, intratracheally, intramuscularly, intracranially, endoscopically, intralesionally, percutaneously, subcutaneously, regionally, or by direct injection or perfusion.

In some embodiments, the oncolytic virus expressing at least one chimeric human/mouse CD40 ligand may be delivered by culturing cells from the patient, infecting the cultured cells with the virus, and reintroducing the infected cells into the patient's body.

A regimen for treatment using the oncolytic virus comprising a gene encoding the at least one chimeric human/mouse CD40 ligand may comprise a single administration or multiple administrations. Multiple administrations may be performed on a recurring schedule and/or in response to one or more indicators of efficacy of one or more prior administrations, or side effects of one or more prior administrations, among others that will be apparent to the person of ordinary skill in the art having the benefit of the present disclosure.

In embodiments wherein the transgene encoding the at least one chimeric human/mouse CD40 ligand is under the control of an inducible promoter, the inducer molecule may be administered to the patient in one administration or in multiple administrations after the one or more administrations of the oncolytic virus comprising the transgene. The inducer molecule may be administered by any route of delivery, such as the routes of delivery described above for the oncolytic virus.

Though not to be bound by theory, an oncolytic virus comprising at least one chimeric human/mouse CD40 ligand may have dual mechanisms of action: 1) tumor cell killing through selective viral replication of the oncolytic virus in cancer cells and 2) induction of systemic anti-tumor immunity generated by both viral immune induction and CD40 ligand immune activation.

In some embodiments, the composition further comprises a pharmaceutically-acceptable carrier. By "pharmaceutically-acceptable" is meant that the carrier is suitable for use in medicaments intended for administration to a patient. The pharmaceutically-acceptable carrier may vary depending on the route of administration, the storage conditions required for a particular oncolytic virus, and other considerations that will be apparent to the person of ordinary skill in the art having the benefit of the present disclosure. In one embodiment, the pharmaceutically-acceptable carrier may be saline.

In still other embodiments, the composition may further comprise an adjuvant, such as an enhancer of viral invasion of a tumor cell, an inducer molecule to induce transcription of the gene encoding the at least one chimeric human/mouse CD40 ligand in constructs wherein the gene is under control of a promoter activated by the inducer molecule, or the like.

Additional Therapies

In some embodiments, the methods may further comprise treatment with an oncolytic virus encoding a chimeric human/mouse CD40 with one or more additional therapies. The additional therapy may be radiation therapy, surgery (e.g., lumpectomy or mastectomy), chemotherapy, gene therapy, DNA therapy, viral therapy, RNA therapy, immunotherapy, biotherapy, bone marrow transplantation, nanotherapy, monoclonal antibody therapy, or a combination of the foregoing. The additional therapy may be in the form of adjuvant or neoadjuvant therapy.

Any one or all of the one or more additional therapies may be administered before, concurrently with, or after administration of the oncolytic virus.

In some embodiments, the additional therapy is the administration of a second virus, such as a virus expressing one or more heterologous proteins. The heterologous proteins may include at least one chimeric human/mouse CD40 ligand. In one embodiment, the second virus is a non-replicating adenovirus encoding MEM40.

Articles of Manufacture of Kits

An article of manufacture or a kit is provided comprising an oncolytic virus encoding a chimeric human/mouse CD40 ligand is also provided herein. The article of manufacture or kit can further comprise a package insert comprising instructions for using the oncolytic virus encoding a chimeric human/mouse CD40 ligand to treat or delay progression of cancer in an individual or to enhance immune function of an individual having cancer. Any of the oncolytic viruses encoding a chimeric human/mouse CD40 ligand described herein may be included in the article of manufacture or kits. Suitable containers include, for example, bottles, vials, bags, and syringes. The container may be formed from a variety of materials such as glass, plastic (such as polyvinyl chloride or polyolefin), or metal alloy (such as stainless steel). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agents include, for example, bottles, vials, bags, and syringes.

The particular embodiments disclosed above are illustrative only, as the disclosure may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the disclosure. Accordingly, the protection sought herein is as set forth in the claims below.

REFERENCES

The following references, to the extent that they provide exemplary procedural or other details supplementary to those set forth herein, are specifically incorporated herein by reference.

Kohlhapp et. al. 2016 Clinical Cancer Research 22(5):1048-1054
Lawler et. al. 2017 JAMA Oncology 3(6):841-849
Macejak et. al. 1991 Nature 353:90-93
Pelletier et. al. 1988 Molecular and Cellular Biology 8(3): 1103-1112
Roizman 1996 PNAS 93:11307-11312
Russell et. al 2014 Nature Biotechnology 30(7):658-670
Singh et. al. 2017 Nature Communications 8(1447):1-10
U.S. Pat. No. 5,925,565
U.S. Pat. No. 7,223,593
U.S. Pat. No. 7,495,090
U.S. Pat. No. 7,928,213
U.S. Pat. No. 5,935,819
van Kooten et. al. 2000 Journal of Leukocyte Biology 67:2-17

What is claimed is:

1. A composition, comprising:
an oncolytic virus comprising a heterologous nucleic acid inserted into the oncolytic virus genome, said nucleic acid comprising a sequence encoding a chimeric human/mouse CD40 ligand operatively linked to a transcriptional control element, wherein the oncolytic virus further comprises one heterologous gene encoding a therapeutic protein, wherein the heterologous gene is selected from the group consisting of genes encoding antibodies, genes encoding pro-drug converting enzymes, and genes encoding checkpoint inhibitors, wherein the chimeric human/mouse CD40 ligand and the therapeutic protein encoded by the one heterologous gene are the only heterologous amino acid sequences expressed by the oncolytic virus.

2. The composition of claim 1, wherein the oncolytic virus is replication competent.

3. The composition of claim 2, wherein the replication competent oncolytic virus is selected from herpes simplex virus (HSV), adenovirus, vaccinia virus, poxvirus, coxsackievirus, poliovirus, measles virus, parvovirus, reovirus, Seneca valley virus, Newcastle disease virus, retrovirus, vesicular stomatitis virus, reovirus, paramyxovirus, Sindbis virus, myxoma virus, Maraba virus, influenza virus, measles virus, mumps virus, arenavirus, and Semliki Forest virus.

4. The composition of claim 3, wherein the replication competent oncolytic virus is a herpes simplex virus.

5. The composition of claim 4, wherein the replication competent oncolytic herpes simplex virus is selected from the group consisting of herpes simplex virus 1 and herpes simplex virus 2.

6. The composition of claim 4, wherein the replication competent oncolytic herpes simplex virus lacks a functional ICP34.5 encoding gene.

7. The composition of claim 6, wherein the nucleic acid comprising a sequence encoding a CD40 agonist operatively linked to a transcriptional control element is inserted in the ICP34.5 encoding gene region.

8. The composition of claim 4, wherein the replication competent oncolytic herpes simplex virus lacks a functional ICP47 encoding gene.

9. The composition of claim 1, wherein the at least one chimeric human/mouse CD40 ligand is selected from the group consisting of ISF30 (SEQ ID NO:1), ISF31 (SEQ ID NO:2), ISF32 (SEQ ID NO:3), ISF33 (SEQ ID NO:4), ISF34 (SEQ ID NO:5), ISF35 (MEM40) (SEQ ID NO:6), ISF36 (SEQ ID NO:7), ISF37 (SEQ ID NO:8), ISF38 (SEQ ID NO:9), ISF39 (SEQ ID NO:10), ISF40 (SEQ ID NO:11), and ISF41 (SEQ ID NO:12).

10. The composition of claim 9, wherein the at least one chimeric human/mouse CD40 ligand is MEM40 (SEQ ID NO:6).

11. The composition of claim 1, wherein the at least one chimeric human/mouse CD40 ligand has at least 90% identity with a ligand selected from the group consisting of ISF30 (SEQ ID NO:1), ISF31 (SEQ ID NO:2), ISF32 (SEQ ID NO:3), ISF33 (SEQ ID NO:4), ISF34 (SEQ ID NO:5), ISF35 (MEM40) (SEQ ID NO:6), ISF36 (SEQ ID NO:7), ISF37 (SEQ ID NO:8), ISF38 (SEQ ID NO:9), ISF39 (SEQ ID NO:10), ISF40 (SEQ ID NO:11), and ISF41 (SEQ ID NO:12).

12. The composition of claim 1, wherein the transcriptional control element operatively linked to the sequence encoding the CD40 agonist is a transcriptional promoter.

13. The composition of claim 12, wherein the transcriptional promoter is a cytomegalovirus (CMV) promoter.

14. The composition of claim 4, wherein the replication competent oncolytic herpes simplex virus is a non-laboratory virus strain.

15. The composition of claim 14, wherein the replication competent oncolytic herpes simplex virus is derived from an HSV JS1 strain.

16. The composition of claim 1, further comprising a pharmaceutically-acceptable carrier.

17. A method, comprising:
administering to a patient suffering from a tumor, an oncolytic virus comprising a heterologous nucleic acid inserted into the oncolytic virus genome, said nucleic acid comprising a sequence encoding a chimeric human/mouse CD40 ligand operatively linked to a transcriptional control element, wherein the oncolytic virus further comprises one heterologous gene encoding a therapeutic protein, wherein the heterologous gene is selected from the group consisting of genes encoding antibodies, genes encoding pro-drug converting enzymes, and genes encoding checkpoint inhibitors, wherein the chimeric human/mouse CD40 ligand and the therapeutic protein encoded by the one heterologous gene are the only heterologous amino acid sequences expressed by the oncolytic virus.

18. The method of claim 17, wherein the oncolytic virus is replication competent.

19. The method of claim 18, wherein the replication competent oncolytic virus is selected from herpes simplex virus (HSV), adenovirus, vaccinia virus, poxvirus, coxsackievirus, poliovirus, measles virus, parvovirus, reovirus, Seneca valley virus, Newcastle disease virus, retrovirus, vesicular stomatitis virus, reovirus, paramyxovirus, Sindbis virus, myxoma virus, Maraba virus, influenza virus, measles virus, mumps virus, arenavirus, and Semliki Forest virus.

20. The method of claim 19, wherein the replication competent oncolytic virus is a herpes simplex virus.

21. The method of claim 20, wherein the replication competent oncolytic herpes simplex virus is selected from the group consisting of herpes simplex virus 1 and herpes simplex virus 2.

22. The method of claim 20, wherein the replication competent oncolytic herpes simplex virus lacks a functional ICP34.5 encoding gene.

23. The method of claim 22, wherein the nucleic acid comprising a sequence encoding a CD40 agonist operatively linked to a transcriptional control element is inserted in the ICP34.5 encoding gene region.

24. The method of claim 20, wherein the replication competent oncolytic herpes simplex virus lacks a functional ICP47 encoding gene.

25. The method of claim 17, wherein the at least one chimeric human/mouse CD40 ligand is selected from the group consisting of ISF30 (SEQ ID NO:1), ISF31 (SEQ ID NO:2), ISF32 (SEQ ID NO:3), ISF33 (SEQ ID NO:4), ISF34 (SEQ ID NO:5), ISF35 (MEMA40) (SEQ ID NO:6), ISF36 (SEQ ID NO:7), ISF37 (SEQ ID NO:8), ISF38 (SEQ ID NO:9), ISF39 (SEQ ID NO:10), ISF40 (SEQ ID NO:11), and ISF41 (SEQ ID NO:12).

26. The method of claim 25, wherein the at least one chimeric human/mouse CD40 ligand is MEM40 (SEQ ID NO:6).

27. The method of claim 17, wherein the at least one chimeric human/mouse CD40 ligand has at least 90% identity to a ligand selected from the group consisting of ISF30 (SEQ ID NO: 1), ISF31 (SEQ ID NO: 2), ISF32 (SEQ ID NO: 3), ISF33 (SEQ ID NO: 4), ISF34 (SEQ ID NO: 5), ISF35 (MEM40) (SEQ ID NO: 6), ISF36 (SEQ ID NO: 7), ISF37 (SEQ ID NO: 8), ISF38 (SEQ ID NO: 9), ISF39 (SEQ ID NO: 10), ISF40 (SEQ ID NO: 11), and ISF41 (SEQ ID NO: 12).

28. The method of claim 17, wherein the transcriptional control element operatively linked to the sequence encoding the CD40 ligand is a transcriptional promoter.

29. The method of claim 28, wherein the transcriptional promoter is a cytomegalovirus (CMV) promoter.

30. The method of claim 20, wherein the replication competent oncolytic herpes simplex virus is a non-laboratory virus strain.

31. The method of claim 30, wherein the replication competent oncolytic herpes simplex virus is derived from an HSV JS1 strain.

32. The method of claim 17, wherein the patient has a cancer selected from primary or metastatic cancer.

33. The method of claim 17, wherein the oncolytic virus is administered intratumorally, intravenously, intraperitoneally, intratracheally, intramuscularly, intracranially, endoscopically, intralesionally, percutaneously, subcutaneously, regionally, or by direct injection or perfusion.

34. The method of claim 17, wherein the oncolytic virus is administered once or multiple times.

35. The method of claim 17, further comprising:
administering at least one additional therapeutic agent.

36. The method of claim 35, wherein the at least one additional therapeutic agent is chemotherapy, immunotherapy, surgery, radiotherapy, viral therapy, or biotherapy.

37. The method of claim 35, wherein the at least one additional therapeutic agent is a nonreplicating adenovirus encoding MEM40.

38. The method of claim 35, wherein the at least one additional therapeutic agent is administered to the patient before administration of the oncolytic virus.

39. The method of claim 35, wherein the at least one additional therapeutic agent is administered to the patient at the same time as administration of the oncolytic virus.

40. The method of claim 35, wherein the at least one additional therapeutic agent is administered to the patient after administration of the oncolytic virus.

41. The method of claim 17, wherein the patient is a human.

42. The composition of claim 1, wherein the heterologous gene is a gene encoding a checkpoint inhibitor.

43. The composition of claim 42, wherein the checkpoint inhibitor is selected from the group consisting of anti-PD-1, anti-CDTA4, and anti-PD-L1.

* * * * *